US010273514B2

(12) United States Patent
Rollie et al.

(10) Patent No.: US 10,273,514 B2
(45) Date of Patent: Apr. 30, 2019

(54) METHOD FOR PREPARING AN AQUEOUS SOLUTION OF BETA-GLUCAN

(71) Applicant: Wintershall Holding GmbH, Kassel (DE)

(72) Inventors: Sascha Rollie, Mannheim (DE); Tobias Käppler, Maxdorf (DE); Carsten Schwalb, Hettenleidelheim (DE); Florian Lehr, Schwegenheim (DE); Andrea Hlubek, Goennheim (DE); Jörg Therre, Worms (DE); Christian Fleck, Sandhausen (DE); Thomas Letzelter, Annweiler (DE); Stephan Freyer, Neustadt (DE); Andrea Herold, Weinheim (DE); Hansjörg Rettenmaier, Bad Duerkheim (DE); Bernd Leonhardt, Bobenheim-Roxheim (DE)

(73) Assignee: Wintershall Holding GmbH, Kassel (DE)

( * ) Notice: Subject to any disclaimer, the term of this patent is extended or adjusted under 35 U.S.C. 154(b) by 0 days.

(21) Appl. No.: 15/532,873

(22) PCT Filed: Dec. 2, 2015

(86) PCT No.: PCT/EP2015/078375
§ 371 (c)(1),
(2) Date: Jun. 2, 2017

(87) PCT Pub. No.: WO2016/087521
PCT Pub. Date: Jun. 9, 2016

(65) Prior Publication Data
US 2017/0362619 A1  Dec. 21, 2017

(30) Foreign Application Priority Data
Dec. 4, 2014 (EP) .................................. 14196214

(51) Int. Cl.
*C12P 19/04* (2006.01)
*C08B 37/00* (2006.01)
*B01D 61/14* (2006.01)

(52) U.S. Cl.
CPC ............ *C12P 19/04* (2013.01); *B01D 61/147* (2013.01); *C08B 37/0024* (2013.01); *B01D 2315/10* (2013.01)

(58) Field of Classification Search
None
See application file for complete search history.

(56) References Cited

U.S. PATENT DOCUMENTS

| 4,667,026 A | 5/1987 | Jarry et al. |
| 4,873,323 A | 10/1989 | Cros et al. |
| 5,010,186 A | 4/1991 | Cros et al. |
| 8,574,873 B2 | 11/2013 | Therre et al. |
| 2016/0002363 A1 | 1/2016 | Therre et al. |

FOREIGN PATENT DOCUMENTS

| CA | 2063490 A1 | 9/1992 |
| CA | 1329159 C | 5/1994 |
| DE | 4012238 A1 | 1/1991 |
| EP | 271907 A2 | 6/1988 |
| EP | 504673 A1 | 9/1992 |
| EP | 463540 B1 | 10/1996 |
| WO | WO-03016545 A2 | 2/2003 |
| WO | WO-2009062561 A1 | 5/2009 |
| WO | WO-2011082973 A2 | 7/2011 |

OTHER PUBLICATIONS

Kang et al. "Effect of air flow rate on scleroglucan synthesis by Sc/erotium glucanicum in an airlift bioreactor with an internal loop" Bioprocess Engineering 23 {2000) 69-74.*
Rau "Glucans secreted by fungi" Turkish Clectronic Journal ofBiotcchnology.*
Dictionary.com "ambient temperature" 2 pgs, copyright 2003-2014.*
U.S. Appl. No. 15/534,597, Briechle et al.
Extended European Search Report for European patent application EP14196214.2 dated Jun. 1, 2015.
International Preliminary Report on Patentability for PCT/EP2015/078375 dated Jun. 15, 2017.
International Search Report and Written Opinion of the International Searching Authority for PCT/EP2015/078375 dated Jan. 11, 2016.

* cited by examiner

*Primary Examiner* — Thane Underdahl
(74) *Attorney, Agent, or Firm* — Drinker Biddle & Reath LLP

(57) ABSTRACT

The presently claimed invention is directed to a method for the preparation of an aqueous solution comprising at least one beta-glucan comprising at least the steps of a) fermentation of at least one fungal strain in an a fermentation broth, b) addition of at least one acid to the fermentation broth to adjust the pH to a value in the range of $\geq 2.0$ to $\leq 4.0$ and c) filtration of the fermentation broth to obtain an aqueous solution comprising the at least one beta-glucan and at least one beta-glucan that is obtained by this method.

11 Claims, No Drawings

METHOD FOR PREPARING AN AQUEOUS SOLUTION OF BETA-GLUCAN

The presently claimed invention is directed to a method for the preparation of an aqueous solution comprising at least one beta-glucan comprising at least the steps of a) fermentation of at least one fungal strain in a fermentation broth, b) addition of at least one acid to the fermentation broth to adjust the pH to a value in the range of $\geq 2.0$ to $\leq 4.0$ and c) filtration of the fermentation broth to obtain an aqueous solution comprising the at least one beta-glucan; and at least one beta-glucan that is obtained by this method.

Beta-glucans are known well-conserved components of cell walls in several microorganisms, particularly in fungi and yeast (Novak, Endocrine, Metabol & Immune Disorders—Drug Targets (2009), 9: 67-75). Biochemically, beta-glucans are non-cellulosic polymers of beta-glucose linked via glycosidic beta(1-3) bonds exhibiting a certain branching pattern with beta(1-6) bound glucose molecules (Novak, loc cit). A large number of closely related beta-glucans exhibit a similar branching pattern such as schizophyllan, scleroglucan, pendulan, cinerian, laminarin, lentinan and pleuran, all of which exhibit a linear main chain of beta-D-(1-3)-glucopyranosyl units with a single betaD-glucopyranosyl unit (1-6) linked to a beta-D-glucopyranosyl unit of the linear main chain with an average branching degree of about 0.3 (Novak, loc cit; EP-B1 463540; Stahmann, Appl Environ Microbiol (1992), 58: 3347-3354; Kim, Biotechnol Letters (2006), 28: 439-446; Nikitina, Food Technol Biotechnol (2007), 45: 230-237). At least two of said beta-glucans—schizophyllan and scleroglucan—even share an identical structure and differ only slightly in their molecular mass, i.e. in their chain length (Survase, Food Technol Biotechnol (2007), 107-118).

Beta-glucans can inter alia be used as thickeners in the field of enhanced oil recovery, in particular in the field of tertiary enhanced oil recovery (EOR; also referred to as tertiary oil recovery, TOR or as improved oil recovery, IOR) (Survase, loc cit).

Suitable thickening polymers for tertiary EOR must meet a number of specific requirements. In addition to sufficient viscosity, the polymers must also be thermally very stable and retain their thickening effect even at high salt concentrations.

An important class of polymers of natural origin for polymer flooding comprises branched homopolysaccharides obtained from glucose, e.g., beta-glucans as described above. Aqueous solutions of such beta-glucans have advantageous physicochemical properties, so that they are particularly suitable for polymer flooding.

Many processes for the preparation of beta-glucans comprise the cultivation and fermentation of microorganisms capable of synthesizing such biopolymers. For example, EP 271 907 A2, EP 504 673 A1 and DE 40 12 238 A1 disclose processes for the preparation, i.e. the preparation is effected by batchwise fermentation of the fungus *Schizophyllum commune* with stirring and aeration. The culture medium substantially comprises glucose, yeast extract, potassium dihydrogen phosphate, magnesium sulfate and water. EP 271 907 A2 describes a method for separating the polysaccharide, in which the culture suspension is first centrifuged and the polysaccharide is precipitated from the supernatant with isopropanol. A second method comprises a pressure filtration followed by an ultrafiltration of the solution obtained, without details of the method having been disclosed. "Udo Rau, "Biosynthese, Produktion and Eigenschaften von extrazellulären Pilz-Glucanen", Habilitationsschrift, Technical University of Brunswick, 1997, pages 70 to 95" and "Udo Rau, Biopolymers, Editor A. Steinbüchel, Volume 6, pages 63 to 79, WILEY-VCH Publishers, New York, 2002" describe the preparation of schizophyllan by continuous or batchwise fermentation. "GIT Fachzeitung Labor 12/92, pages 1233-1238" describes a continuous preparation of branched beta-1,3-glucans with cell recycling. WO 03/016545 A2 discloses a continuous process for the preparation of scleroglucans using *Sclerotium rolfsii*.

It is essential that an aqueous solution comprising at least one beta-glucan that is used for polymer flooding does not comprise any gel particles or other small particles at all. Even a small number of particles having dimensions in the micron range blocks the fine pores in the mineral oil-containing formation and thus at least complicates or even stops the mineral oil production.

Consequently it is therefore also important that aqueous solutions containing at least one beta-glucan are substantially free of cells and cell fragments because these cells and/or cell fragments otherwise block the mineral oil formation which complicates the extraction of the mineral oil or even makes it impossible. The so-called Filtration Ratio (FR value) can be used for characterizing the quality of aqueous solutions comprising at least one beta-glucan.

In principle the removal of cell fragments, gel particles and other small particles could be improved by using filter membranes with a small pore size. With decreasing pore size, however, the filter membranes increasingly also retain the beta-glucans, in particular the fractions of the beta-glucans that have very high molecular weights. The retention of beta-glucans with a very high molecular weight leads to a loss of beta-glucans and makes the overall process for the production of beta-glucans less economical.

U.S. Pat. No. 5,010,186 and U.S. Pat. No. 4,873,323 A disclose polysaccharide biopolymers having improved filterability that are prepared by acidifying an aqueous polysaccharide composition with nitric acid to a pH value from about 2 to 0.1 and treating said acidified composition at a temperature from about 50° C. to 100° C. for about 5 to 60 minutes.

U.S. Pat. No. 4,667,026 A describes an aqueous solution of polysaccharide biopolymers that are heat treated for more than 5 minutes at a pH value ranging from 3.5 to 6.2 to improve the filterability thereof.

WO 2011/082973 A2 describes a method for producing aqueous solutions of glucans by fermenting fungus strains secreting said glucans into the fermentation broth in an aqueous culture medium, wherein the separation of the glucans from the fermentation broths takes place by means of asymmetric filter membranes.

WO 2009/062561 A1 provides a process for the preparation of glucans comprising the steps of providing an aqueous glucan initial solution having a pH of above 11.0, filtering the aqueous glucan initial solution to obtain a glucan containing filtrate, adjusting the pH of the glucan containing filtrate with an acid to a pH of below 5.0 to obtain an acidic glucan solution and heating the acidic glucan solution to a temperature in the range of 60 to 160° C.

Accordingly, it was an object of the presently claimed invention to provide an economical process for the preparation of an aqueous solution comprising at least one beta-glucan with improved quality as assessed by a low FR value, in particular a FR value $\leq 2.0$, as determined with a membrane having a pore size of 1.2 µm.

Surprisingly, it was found that the addition of at least one acid to a fermentation broth containing at least one beta-glucan to adjust the pH to a value in the range of $\geq 2.0$ to $\leq 4.0$ at a temperature of ≥15 to ≤50° C. just prior to further processing of the broth, for example by microfiltration, led to the reduction of the FR value of an aqueous solution containing beta-glucan after filtration, in particular to a level ≤2.0 as determined with a membrane having a pore size of 1.2 µm, thereby allowing to obtain an aqueous solution containing at least one-beta glucan with improved quality that is suitable for using in enhanced oil recovery.

Thus, in one embodiment, the presently claimed invention is directed to a method for the preparation of an aqueous solution comprising at least one beta-glucan comprising at least the steps of:

a) fermentation of at least one fungal strain which secretes the at least one beta-glucan into an aqueous culture medium to obtain a fermentation broth comprising the at least one beta-glucan, the water and biomass, b) addition of at least one acid to the fermentation broth obtained in step a) to adjust the pH to a value in the range of ≥2.0 to ≤4.0 and c) filtration of the fermentation broth obtained in step b) to obtain an aqueous solution comprising the at least one beta-glucan.

Thus, in another embodiment, the presently claimed invention is directed to a method for the preparation of an aqueous solution comprising at least one beta-glucan comprising at least the steps of:

a) fermentation of at least one fungal strain which secretes the at least one beta-glucan into an aqueous culture medium to obtain a fermentation broth comprising the at least one beta-glucan, the water and biomass, b) addition of at least one acid to the fermentation broth obtained in step a) to adjust the pH to a value in the range of ≥2.0 to ≤4.0 while maintaining the temperature of the fermentation broth in the range of ≥15 to ≤55° C. and c) filtration of the fermentation broth obtained in step b) to obtain an aqueous solution comprising the at least one beta-glucan.

The single steps of the method according to the presently claimed invention and details concerning the presently claimed invention will be explained in detail in the following.

Beta-glucans are a heterogeneous group of glucose polymers found in the cell walls of plants, bacteria and fungi. The common basic structural unit in beta-glucan as described herein is a backbone chain and side chains comprising or consisting of beta-(1-3)-linked glucosyl units. Depending on the source and method of isolation, beta-glucans have various degrees of branching and linkages in the side chains.

Generally, in context with the presently claimed invention, the beta-glucan as described herein may be any beta-glucan such as beta-1,4-glucans, beta-1,3-glucans, beta-1,6-glucans and beta-1,3(1,6)-glucans. In one embodiment, the beta-glucan is a polymer consisting of a linear main chain of beta-D-(1-3)-glucopyranosyl units having a single beta-D-glucopyranosyl unit (1-6) linked to a beta-D-glucopyranosyl unit of the linear main chain with an average branching degree of about 0.3. In context with the presently claimed invention, the term average branching degree about 0.3" means that in average about 3 of 10 beta-D-(1-3)-glucopyranosyl units are (1-6) linked to a single beta-D-glucopyranosyl unit. In this context, the term about" means that the average branching degree may be within the range from 0.25 to 0.35, preferably from 0.25 to 0.33, more preferably from 0.27 to 0.33, most preferably from 0.3 to 0.33. It may also be 0.3 or 0.33. Schizophyllan and scleroglucan have an average branching degree between 0.25 and 0.33 (Novak, loc cit, Survase, loc cit); for example, scleroglucan and schizophyllan have an average branching degree of 0.3 to 0.33. The average branching degree of a beta-glucan can be determined by methods known in the art, e.g., by periodic oxidation analysis, methylated sugar analysis and NMR (Brigand, Industrial Gums, Academic Press, New York/USA (1993), 461-472).

In the context of the presently claimed invention, the at least one beta-glucan to be produced as described herein is preferably selected from the group consisting of schizophyllan and scleroglucan, particularly preferably the at least one beta-glucan is schizophyllan.

Schizophyllan and scleroglucan can both be referred to as beta-1,3-glucans. The polysaccharide chains usually form a three-dimensional structure of triple helices; polymer chains consist of glucose units whose hydroxy groups in 1- and 3-position are beta-linked to form the polymer main chain, and wherein each third glucose unit contains in position 6 a further glucose moiety linked by its hydroxyl function in position 1 (beta-1,3-bonded glucopyranose as the main chain and beta-1,6-bonded glucopyranose as side chains) and has the structural formula:

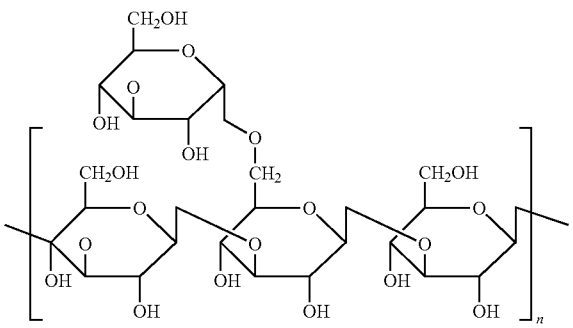

wherein n is a number which provides the beta-1,3-glucan component with a weight average molecular weight (Mw) of $1 \cdot 10^6$ g/mol to $12 \cdot 10^6$ g/mol, preferably $2 \cdot 10^6$ g/mol to $10 \cdot 10^6$ g/mol.

All weight average molecular weights (Mw) are determined from the readily measured Staudinger index q using the following Mark-Houwink equation:

$$Mw=[\eta/4 \cdot 45 \cdot 10^{-7}]^{1/1.49}.$$

Beta-1,3-glucans-secreting strains of fungi are known to those skilled in the art. The strains of fungi are preferably selected from the group consisting of *Schizophyllum commune*, *Sclerotium rolfsii* and *Sclerotium glucanicum*. Suitable strains of fungi are also mentioned, for example, in EP 271 907 A2 and EP 504 673 A1, in each case claim 1. The strain of fungus used to produce the inventively used beta-glucan is particularly preferably *Schizophyllum spec* or *Sclerotium spec*, very particularly preferably *Schizophyllum commune* or *Sclerotium rolfsii* and most particularly preferably *Schizophyllum commune*. This strain of fungus secretes a glucan in which, on a main chain composed of β-1,3-glycosidically linked glucose units, each third unit, statistically, of the main chain is β-1,6-glycosidically linked to a further glucose unit; i.e. the glucan is preferably schizophyllan.

Thus, in another embodiment, the presently claimed invention is directed to a method for the preparation of an aqueous solution comprising schizophyllan comprising at least the steps of:

a) fermentation of at least one fungal strain which secretes schizophyllan into an aqueous culture medium to obtain a fermentation broth comprising schizophyllan, the water and biomass, b) addition of at least one acid to the fermentation broth obtained in step a) to adjust the pH to a value in the range of ≥2.0 to ≤4.0 and c) filtration of the fermentation broth obtained in step b) to obtain an aqueous solution comprising schizophyllan.

Thus, in another preferable embodiment, the presently claimed invention is directed to a method for the preparation of an aqueous solution comprising schizophyllan comprising at least the steps of:

a) fermentation of at least one fungal strain which secretes schizophyllan into an aqueous culture medium to obtain a fermentation broth comprising schizophyllan, the water and biomass, b) addition of nitric acid to the fermentation broth obtained in step a) to adjust the pH to a value in the range of ≥2.0 to ≤4.0 and c) filtration of the fermentation broth obtained in step b) to obtain an aqueous solution comprising schizophyllan.

Thus, in another embodiment, the presently claimed invention is directed to a method for the preparation of an aqueous solution comprising schizophyllan comprising at least the steps of:

a) fermentation of at least one fungal strain which secretes schizophyllan into an aqueous culture medium to obtain a fermentation broth comprising schizophyllan, the water and biomass, b) addition of at least one acid to the fermentation broth obtained in step a) to adjust the pH to a value in the range of ≥2.0 to ≤4.0 while maintaining the temperature of the fermentation broth in the range of ≥15 to ≤55° C. and c) filtration of the fermentation broth obtained in step b) to obtain an aqueous solution comprising schizophyllan.

Thus, in another preferable embodiment, the presently claimed invention is directed to a method for the preparation of an aqueous solution comprising schizophyllan comprising at least the steps of:

a) fermentation of at least one fungal strain which secretes schizophyllan into an aqueous culture medium to obtain a fermentation broth comprising schizophyllan, the water and biomass, b) addition of nitric acid to the fermentation broth obtained in step a) to adjust the pH to a value in the range of ≥2.0 to ≤4.0 while maintaining the temperature of the fermentation broth in the range of ≥15 to ≤55° C. and c) filtration of the fermentation broth obtained in step b) to obtain an aqueous solution comprising schizophyllan.

Step a):

The fermentation broth is obtained by fermenting fungi in a suitable aqueous nutrient medium. During the course of the fermentation, the fungi secrete the abovementioned class of glucans into the aqueous fermentation broth.

Processes for the fermentation of such strains of fungi are known in principle to those skilled in the art, for example from EP 271 907 A2, EP 504 673 A1, DE 40 12 238 A1, WO 2003/016545 A2 and also "Udo Rau, "Biosynthese, Produktion and Eigenschaften von extrazellulären Pilz-Glucanen", Habilitationsschrift, Technical University of Braunschweig, 1997", which in each case also mention suitable nutrient media. The fermentation systems may be continuous or batchwise systems.

According to the invention, the fungi can be cultured, for example, in an aqueous culture medium at a temperature of from 15° C. to 40° C., preferably from 25 to 30° C. and, for example, at about 27° C., preferably with aeration and flow, for example using a stirrer.

In the method according to the invention, the fermentation should preferably be run in such a way that the concentration of the glucans to be prepared is at least 2 g/l in the fermentation broth to be filtered. The upper limit is in principle not limited. It depends on the viscosity which can still be handled by the fermentation apparatus used in each case. However, the fermentation broth obtained in step a) contains preferably to 50 g beta-glucan per liter of aqueous solution and more preferably to 40 g beta-glucan per liter of aqueous solution.

Step b):

Preferably the at least one acid is added to the fermentation broth when the fermentation has been completed.

Preferably the at least one acid is selected from the group consisting of at least one inorganic acid and at least one organic acid. Preferably the at least one inorganic acid is selected from the group consisting of hydrochloric acid, nitric acid, phosphoric acid, sulphuric acid, boric acid, hydrofluoric acid, hydrobromic acid and perchloric acid. Preferably the at least one organic acid is selected from the group consisting of lactic acid, acetic acid, formic acid, citric acid, oxalic acid, uric acid, benzoic acid and malic acid.

More preferably the at least one acid is selected from the group consisting of nitric acid, formic acid and phosphoric acid, most preferably the at least one acid is nitric acid.

Preferably the pH of the filtration broth is adjusted to a value in the range of ≥2.5 to ≤4.0, more preferably in the range of ≥3.0 to ≤4.0.

Preferably the at least one acid is added to the fermentation broth in step b) at a temperature in the range of ≥15 to ≤50° C., more preferably at a temperature in the range of ≥15 to ≤40° C., even more preferably at a temperature in the range of ≥20 to ≤35° C., most preferably at a temperature in the range of ≥25 to ≤30° C.

Preferably the temperature of the fermentation broth in step b) is maintained at a temperature in the range of ≥15 to ≤50° C., more preferably at a temperature in the range of ≥15 to ≤40° C., even more preferably at a temperature in the range of ≥20 to ≤35° C., most preferably at a temperature in the range of ≥25 to ≤30° C., during the addition of the at least one acid.

Preferably the amount of the at least one acid in step b) is added completely or in several parts until the desired pH value is achieved. The at least one acid is preferably added as an aqueous solution by using suitable dosing equipment. The at least one acid is preferably added when the level of glucose in the fermentation broth has fallen below a certain level.

Preferably the pH value of the fermentation broth is monitored by means of pH probe during the addition of the at least one acid. Preferably, the fermentation broth is mixed with the at least one acid for a period of 1 to 60 min, more preferably 1 to 30 min, even more preferably 1 to 20 min and most preferably 1 to 10 min before the fermentation broth is subjected to filtration.

Step c):

Finally, an aqueous solution comprising at least one beta-glucan is separated by crossflow microfiltration from the fermentation broth which comprises at least one beta-glucan and biomass (fungal cells with or without cell constituents), so that an aqueous fermentation broth in which the biomass has a higher concentration than beforehand remains.

Preferably, the fermentation is carried out in a fermenter. After the fermentation is terminated, the fermenter content is filtered with the use of asymmetrical filter membranes or symmetrical filter membranes. Further work-up of the aqueous solution with reduced biomass concentration containing at least one beta-glucan can follow, like further concentration steps.

Alternatively, the fermentation is carried out in a suitable plant which comprises at least one fermenter. The fermentation broth is removed continuously or from time to time from the fermenter via a side stream and an aqueous solution comprising at least one beta-glucan is separated off therefrom by crossflow microfiltration. The remaining aqueous fermentation broth in which the biomass has a higher concentration than beforehand can be at least partly recycled to the fermentation container. Further work-up of the aqueous solution with reduced biomass concentration containing at least one beta-glucan can follow, like further concentration steps.

The crossflow microfiltration process is known in principle to the person skilled in the art and is described, for example, in "Melin, Rautenbach, Membranverfahren, Springer-Verlag, 3rd edition, 2007, page 309 to page 366". Here, "microfiltration" is understood by the person skilled in the art as meaning the removal of particles having a size of from about 0.1 µm to about 10 µm.

In the crossflow filtration, a stream of the liquid to be filtered is applied, for example, by a suitable circulation pump, parallel to the surface of the membrane used as filtration material. A liquid stream therefore continuously flows over the filter membrane, and the formation of deposits on the membrane surface is prevented or at least reduced thereby. In principle, all types of pumps are suitable. Owing to the high viscosity of the medium to be transported, however, in particular positive displacement pumps and very particularly eccentric screw pumps and rotary piston pumps have proven useful.

Preferably asymmetrical filter membranes or symmetrical tubular membranes are used for the crossflow microfiltration. Asymmetrical filter membranes consist of at least two different layers having different pore size, i.e. of at least one support layer and one separating layer. The support layer is comparatively thick and has comparatively large pores. It imparts the mechanical strength to the filter membrane. At least one separating layer having finer pores than the pores of the support layer is applied to the support layer. Optionally, one or more intermediate layers may also be arranged between the separating layer and the support layer. The asymmetrical membranes may be, for example, metallic membranes or ceramic membranes. The asymmetrical membranes used are preferably asymmetrical ceramic membranes. Details of asymmetrical ceramic membranes are described, for example, in "Melin, Rautenbach, Membranverfahren, Springer-Verlag, 3rd edition, 2007, page 51 to page 52".

Symmetrical tubular membranes are tubular membranes which have a pore distribution which is essentially constant over the entire cross section of the membrane wall. Symmetrical tubular membranes are known to those skilled in the art and are described, inter alia, in "Melin, Rautenbach, Membranverfahren, Springer-Verlag, 3rd edition, 2007, page 20".

Preferably the temperature of the fermentation broth is maintained below 60° C., more preferably below 55° C. and even more preferably below 50° C. when carrying out the steps a), b) and c) of the inventively claimed method.

By means of the method according to the invention, an aqueous solution comprising at least one beta-glucan which is suitable for tertiary mineral oil production can be prepared in a simple and highly economical manner.

The inventively claimed method to prepare an aqueous solution containing at least one beta-glucan does not alter the three-dimensional structure of the at least one beta-glucan, e.g. by modifying its tertiary structure. Thus, the inventively claimed aqueous solution comprising at least one beta-glucan shows a viscosity that is identical or similar to the viscosity of an aqueous solution that is containing at least one beta-glucan in the same amount that was not prepared by the inventively claimed method. Hence, the inventively claimed aqueous solution comprising at least one beta-glucan exhibits the same degree of effectiveness or a higher degree of effectiveness compared to an aqueous solution that is containing at least one beta-glucan in the same amount that was not prepared by the inventively claimed method, if used for the purposes of enhanced oil recovery.

Thus, in another embodiment, the presently claimed invention is directed to an aqueous solution of at least one beta-glucan which is obtainable by the inventively claimed method.

The good quality of the aqueous solution comprising at least one beta-glucan is evident from the good filtration properties, which are expressed by the low filtration ratio (FR value). The FR value of the product is preferably in the range of $\geq 1.0$ to $\leq 2.0$, more preferably in the range of $\geq 1.0$ to $\leq 1.8$, even more preferably in the range of $\geq 1.0$ to $\leq 1.3$, as in each case determined by using a membrane having a pore size of 1.2 µm.

The yield of at least one beta-glucan after filtration, i.e. the amount of at least one beta-glucan which can be recovered from the fermentation broth, based on the amount of at least one beta-glucan present in the fermentation broth prior to filtration, is preferably in the range from $\geq 25\%$ to $\leq 97\%$, more preferably in the range from $\geq 30\%$ to $\leq 95\%$ and most preferably in the range from $\geq 50\%$ to $\leq 93\%$.

The aqueous solution containing at least one beta-glucan may be further worked up and concentrated in order to obtain the at least one beta-glucan in highly concentrated form. For example, the aqueous solution comprising at least one beta-glucan can be contacted with at least one precipitating agent to obtain at least one precipitated beta-glucan in a solvent mixture comprising water and the at least one precipitating agent. Preferably, the at least one precipitating agent is selected from the group consisting of low boiling liquids, high boiling liquids and mixtures thereof. Examples of low boiling liquids are formates like methyl formate, acyclic ethers like dimethoxymethane, cyclic ethers like tetrahydrofuran, 2-methyl-1,2-dioxalane, carboxylic acid esters like acetic acid ethyl ester, alcohols like methanol, ethanol, isopropanol or propanol, ketones like acetone or methylethylketone, or mixtures of at least two of them. Examples of high boiling liquids are polyethylene glycols having molecular weights preferably in the range of 10 to 200 kD, more preferably in the range of 15 to 120 kD, polypropylene glycols having molecular weights in the range of 5 to 100 kD, more preferably 10 to 30 kD, or mixtures of at least two of them. The at least one precipitating agent is generally added to the aqueous solution comprising at least one beta-glucan, so that the volume ratio of the precipitating agent to the aqueous solution is in the range of preferably 0.1:1 to 20:1, more preferably 0.2:1 to 2:1, most preferably 0.2:1 to 1.5:1, in each case based on the total mixture that is obtained.

The at least one precipitated beta-glucan can be separated from the solvent mixture comprising water and the at least one precipitating agent to obtain a precipitated beta-glucan in highly concentrated form. The separation can in general be conducted by any methods known to the skilled artisan, for example, inter alia, centrifugation, sedimentation, flotation and filtration.

The beta-glucan such as schizophyllan which is obtained according to the inventively claimed method may be further modified after filtration and optionally concentration. The beta-glucan such as schizophyllan can also be chemically, enzymatically or physically modified. For example, the beta-glucan such as schizophyllan may be converted by oxidation, enzyme conversion, acid hydrolysis, heat and/or acid dextrinization or shear. Suitable chemical derivatives of schizophyllan include esters, such as the acetate and half esters, such as the succinate, octenyl succinate and tetradecenyl succinate, phosphate derivatives, ethers such as hydroxyalkyl ethers and cationic ethers, or any other derivatives or combinations thereof. Modification may also be chemical crosslinking. Crosslinking agents that are suitable for use herein include phosphorus oxychloride, epichlorohydrin, sodium trimetaphosphate and adipic acid/acetic acid mixed anhydrides.

The following examples are intended to illustrate the invention in more detail:

EXAMPLES

1. Determination of the Filtration Ratio (FR Value)
Principle of Measurement:
In the determination of the filtration ratio (FR value), the amount of filtrate which runs through a defined filter is determined as a function of time. The FR value is determined according to the following formula (I)

$$FR = (t_{190\,g} - t_{170\,g})/(t_{70\,g} - t_{50\,g}) \quad (I),$$

where the variables and the equation have the following meaning:
$t_{190\,g}$ = time in which 190 g of filtrate are obtained,
$t_{170\,g}$ = time in which 170 g of filtrate are obtained,
$t_{70\,g}$ = time in which 70 g of filtrate are obtained,
$t_{50\,g}$ = time in which 50 g of filtrate are obtained.

Thus, in each case the time span which is required for in each case 20 g of filtrate to flow through the filter is determined, i.e. at an early time and at a late time in the filtration process, and the quotient is calculated from the two time spans. The larger the FR value, the higher the decrease in filtration velocity with increasing duration of the filtration process. This indicates increasing blockage of the filter, for example by gels or particles.

The FR value is determined by the following method:
1.1. Equipment
a) Sartorius pressure filtration apparatus 16249; filter diameter 47 mm; with 200 ml digestion cylinder (Øi=41 mm)
b) Isopore membrane 1.2 µm; Ø47 mm; No. RTTP04700 available from Merck Millipore
c) Balance 1.2. Preparation of the Glucan Solution
First, 50 g of a mixture of the glucan solution obtained from the experiments and water is prepared, i.e. in a ratio such that the concentration of the glucan is 1.75 g/l. The mixture is stirred for 10 min and checked visually for homogeneity. If the mixture is still inhomogeneous, further stirring is effected until the mixture is homogeneous. The mixture is then made up to a total amount of 250 g with 200 g of ultrapure water. Thereafter, stirring is effected for at least 1 h for homogenization, after which the pH is adjusted to 6.0 with 0.1 M NaOH and stirring is then effected again for 15 min. The pH of 6.0 is checked again. The final concentration of the glucan in the mixture is 0.35 g/l.

1.3. Carrying Out the Filtration Test
The filtration test is effected at room temperature (T=25° C.) at a pressure of 1.0 bar (compressed air or $N_2$).
  place coarse support grid on the sieve tray
  place fine support grid on the sieve tray
  place membrane filter on top
  insert seal (O-ring)
  screw sieve tray and outlet tap to the cylinder
  close outlet tap
  introduce 220 g (about 220 ml) of solution
  screw upper cover to cylinder
  clamp on inlet air tube
  check pressure and adjust to 1.0 bar
  place beaker on the balance under the filtration apparatus. Press tare.
  open outlet tap
  the test is stopped when no more filtrate emerges.

By means of the balance, the amount of filtrate is determined as a function of time. The mass indicated in each case can be read visually but of course also automatically and evaluated.

2. Preparation of the Fermentation Broth, Acidification and Determination of the FR Value and the Viscosity Schizophyllum commune was used for the experiments and schizophyllan was produced in a batch fermentation at a temperature of about 24° C. as described in "Udo Rau, Biopolymers, edited by A. Steinbüchel, WILEY-VCH publishers, Volume 6, pages 63 to 79".

At the end of the fermentation process an aqueous solution of $HNO_3$ (53 wt % $HNO_3$) was added to the reactor containing the fermentation broth via a pipeline. The pH value was measured by using an installed pH value probe and the temperature was measured by means of a sensor. The aqueous solution of $HNO_3$ was added at a rate that allows to maintain the temperature of the fermentation broth in the range of 28 to 32° C. Usually the addition of the aqueous solution of $HNO_3$ took place during a period of 2 to 10 min.

The FR value is determined as described above.

The viscosity of the aqueous solution containing schizophyllan is determined at a concentration of 0.35 g/l at a temperature of 25° C. and a shear rate of 7 $s^{-1}$ with a ThermoScientific HAAKE™ RheoStress™ (plate/cone PP60H/C60/1° Ti) in a solution containing salts (NaCl 132, $MgCl_2$ 10.5, $CaCl_2$ 42.6, $Na_2SO_4$ 0.27 and $NaBO_2$ 0.182, in each case g/L).

| example | amount fermentation broth [m³] | concentration schizophyllan [g/L] | amount aqueous solution of $HNO_3$ (53 wt. % $HNO_3$) [kg] | pH before filtration | FR at pH 6 | Viscosity at 7 $s^{-1}$ [mPa · s] |
|---|---|---|---|---|---|---|
| 1 | 100 | 5.3 | 100 | 3.87 | 1.17 | 30.5 |
| 2 | 95 | 6.3 | 95 | 3.68 | 1.21 | 29.4 |
| 3 | 93 | 5.2 | 102 | 3.24 | 1.24 | 36.2 |
| 4 | 93 | 4.9 | 110 | 3.39 | 1.16 | 36.5 |

-continued

| example | amount fermentation broth [m³] | concentration schizophyllan [g/L] | amount aqueous solution of HNO₃ (53 wt. % HNO₃) [kg] | pH before filtration | FR at pH 6 | Viscosity at 7 s⁻¹ [mPa·s] |
|---|---|---|---|---|---|---|
| 5* | 89 | 5.5 | 0 | 4.21 | 3.65 | 33.0 |
| 6* | 88 | 5.6 | 0 | 4.21 | 2.57 | 36.4 |

*= comparative examples

When the pH value of the fermentation broth was lowered ≤2.0, the cells dissolved by means of lysis. The presence of cell walls and cell contents has a negative impact on the FR value. The solutions containing schizophyllan that was prepared according to the inventively claimed process have a very good quality as evidenced by their low FR value and are suitable for the use in enhanced oil recovery applications as evidenced by their high viscosity.

The invention claimed is:

1. A method for the preparation of an aqueous solution comprising at least one beta-glucan comprising:
    a) fermenting at least one fungal strain which secretes the at least one beta-glucan into an aqueous culture medium to obtain a fermentation broth comprising the at least one beta-glucan, the water and biomass,
    b) adding at least one acid to the fermentation broth obtained in step a) to adjust the pH to a value in the range of ≥3.0 to ≤4.0 while maintaining the temperature of the fermentation broth in the range of ≥15 to ≤55° C. and
    c) filtering the fermentation broth obtained in step b) to obtain an aqueous solution comprising the at least one beta-glucan.

2. The method according to claim 1, wherein the concentration of the at least one beta-glucan in the fermentation broth obtained in step a) is in the range of ≥2 to ≤50 g beta-glucan per liter of fermentation broth.

3. The method according to claim 1, wherein the at least one beta-glucan is selected from the group consisting of schizophyllan and scleroglucan.

4. The method according to claim 1, wherein the fungal strains are *Schizophyllum* spec or *Sclerotium* spec.

5. The method according to claim 1, wherein the fermentation is carried out at a temperature in the range of ≥15 to ≤40° C. with aeration and flow.

6. The method according to claim 1, wherein the at least one acid is selected from the group consisting of at least one inorganic acid and at least one organic acid.

7. The method according to claim 6, wherein the at least one inorganic acid is selected from the group consisting of hydrochloric acid, nitric acid, phosphoric acid, sulphuric acid, boric acid, hydrofluoric acid, hydrobromic acid and perchloric acid.

8. The method according to claim 6, wherein the at least one organic acid is selected from the group consisting of lactic acid, acetic acid, formic acid, citric acid, oxalic acid, uric acid and malic acid.

9. The method according to claim 1, wherein the at least one acid is added to the fermentation broth while maintaining the temperature of the fermentation broth in the range of ≥15 to ≤40° C.

10. The method according to claim 1, wherein the filtering is a crossflow microfiltration.

11. The method according to claim 1, wherein the filtering is carried out at a temperature in the range of ≥15 to ≤40° C.

* * * * *